(12) United States Patent
Keyes (10) Patent No.: US 12,089,700 B2
(45) Date of Patent: Sep. 17, 2024

(54) FOOT FEATURE MEASUREMENT AND SIMULATION

(71) Applicant: Larry Keyes, Oak Park, IL (US)

(72) Inventor: Larry Keyes, Oak Park, IL (US)

( * ) Notice: Subject to any disclaimer, the term of this patent is extended or adjusted under 35 U.S.C. 154(b) by 566 days.

(21) Appl. No.: 17/027,150

(22) Filed: Sep. 21, 2020

(65) Prior Publication Data
US 2021/0085033 A1 Mar. 25, 2021

Related U.S. Application Data

(60) Provisional application No. 62/904,228, filed on Sep. 23, 2019.

(51) Int. Cl.
| | | |
|---|---|---|
| *A43D 1/02* | (2006.01) | |
| *A61B 5/103* | (2006.01) | |
| *A61B 5/107* | (2006.01) | |
| *G01B 5/02* | (2006.01) | |
| *G01B 11/02* | (2006.01) | |

(52) U.S. Cl.
CPC ............. *A43D 1/022* (2013.01); *A43D 1/025* (2013.01); *A61B 5/103* (2013.01); *A61B 5/107* (2013.01); *A61B 5/1071* (2013.01); *A61B 5/1072* (2013.01); *A61B 5/1074* (2013.01); *A61B 5/1079* (2013.01); *G01B 5/02* (2013.01); *G01B 11/02* (2013.01)

(58) Field of Classification Search
CPC ........ A43D 1/022; A43D 1/025; A43D 1/027; A61B 5/103; A61B 5/107; A61B 5/1071; A61B 5/1072; A61B 5/1074; A61B 5/1079; G01B 5/02; G01B 11/02
See application file for complete search history.

(56) References Cited

U.S. PATENT DOCUMENTS

| | | | | |
|---|---|---|---|---|
| 6,654,705 | B1* | 11/2003 | Benson | A43D 1/025 702/152 |
| 7,153,457 | B2* | 12/2006 | Shor | A43D 3/021 264/156 |
| 7,343,691 | B2* | 3/2008 | Long | A43D 1/06 33/3 R |
| 7,757,325 | B2* | 7/2010 | Cook | A43B 23/0205 12/145 |
| 2002/0157266 | A1* | 10/2002 | Dowdell | A43D 1/02 33/515 |
| 2004/0073407 | A1* | 4/2004 | Nguyen | A43D 1/025 702/194 |
| 2010/0130830 | A1* | 5/2010 | Lin | G16H 40/60 600/300 |
| 2018/0149460 | A1* | 5/2018 | McGuire | G01B 3/008 |

* cited by examiner

*Primary Examiner* — Devin B Henson
(74) *Attorney, Agent, or Firm* — Amundsen Davis, LLC (57) ABSTRACT

A method comprises arranging a measurement paper. The measurement paper may include a plurality of lines to aid in centering a foot. The method may further include tracing a foot onto the measurement paper and making a plurality of measurements on the traced foot. Based on the plurality of measurements, shoe fit evaluator may be constructed.

18 Claims, 7 Drawing Sheets

FOOT FEATURE MEASUREMENT AND SIMULATION

PRIORITY CLAIM

This application claims priority to U.S. Provisional Patent Application No. 62/904,228, filed Sep. 23, 2019, the contents of which are hereby incorporated by reference.

BACKGROUND OF THE INVENTION

Footwear is worn by nearly every person for a number of hours on nearly every day. As such, it is important that a person's footwear not only be comfortable but fit correctly. Incorrect fit can lead to foot problems which may require further correction and treatment later on.

DETAILED DESCRIPTION

The importance of footwear fit cannot be overstated. Properly fitting footwear can not only assist in addressing existing foot problems, such as bunions and hammer toes, but can also help prevent future problems caused by forcing one's foot into ill-fitting shoes. When purchasing shoes, one often has their foot size measured; however, this provides an incomplete profile of the foot by primarily focusing on the length as measured from heel to big toe.

One way to attempt to provide a more complete foot profile is to perform a measurement of the foot that uses additional measurements beyond length. For example, a foot may have its width and depth measured, in addition to its length, in order to provide several measurement values for the same foot. Width and depth are, of course, important measurements to consider when determining what shoes to purchase, as some shoes are better for wider or narrower feet, or have additional depth. However, the measurement of length, width, and depth is often too crude; that is, measuring a foot with only those measurements may not accurately capture the unique features and issues with a person's fit. In many instances, a person may only have a significant issue with their foot, and thus with shoes, in a particular area of the foot, for example, the toes. While a length, width, and depth measurement may account for some of the issues with the foot, other issues may be unable to be accurately captured with those measurements, meaning that a person will be unable to use the information to help select the best fitting pair of shoes.

Another way to aid in shoe fit selection is to measure the shoe itself. Often, this is done by scanning the interior of a shoe and using the scan as the basis of a model for the shoe. However, as with the basic measurement of the foot, measurement of the shoe itself may not be sufficient to aid a person in selecting the best-fitting shoe for their foot. First, a consumer may not have sufficient knowledge to select the shoe that will work for their foot—or, conversely, eliminate a shoe from consideration—based on a scan of the interior of the shoe. Without an awareness of how the interior features of the shoe will interact with their particular foot and foot features, a person may simply not know how to translate a scan of a shoe's interior into a determination as to whether or not the shoe is a good match. In addition, because a person may only have an issue with a specific area of their foot, measuring the interior of a shoe may lead to false exclusions of a shoe that may otherwise work. For example, a person may know that they have an issue with their toe area and thus exclude shoes that, based on their internal scans, appear to have a narrow toe box. However, depending on the structure of the shoe in relation to the person's foot, the shoe with the narrow-appearing toe box may actually be a good fit for the person. With no way to test the shoe (apart from trying it on, which provides a limited sample), a person may be unnecessarily excluding shoes.

One way to combat the shortcomings of the individual approaches of foot measurement and shoe interior mapping is to combine the two approaches. One form this may take is inputting a person's foot length, width, and height measurements into a database, where the database also contains information corresponding to a variety of shoes that have had their interior features scanned. The measurements of the foot may then be digitally compared with, or "inserted" into, the shoe in order to help a person determine whether the shoe is likely to be a good fit. While this approach seems good at first glance, it does suffer from several problems. The first is that combining the foot measurement and shoe interior scan is cumbersome. If performed at a retail establishment, i.e., at the point of sale, a person would need to go through the steps of having their feet measured and then compared to a database of shoe interiors. This requires additional work on the part of the employees to perform a full set of measurements, as opposed to just a length measurement, which a retail employee may not be fully trained to do. Relatedly, performing these measurements at a retail location would necessitate additional equipment to perform the measurements, as opposed to a standard Brannock device currently used to measure length. The measurement concerns may be addressed by, for example, having the measurements performed at a doctor's office; however, doing the measurement at a separate location introduces additional steps, including printing out the measurements for the patient and having the patient bring the measurements with them every time they want to purchase a new pair of shoes. Moreover, in order to be truly comprehensive, every pair of available shoes would need to be scanned, even if it would be unlikely that one patient would buy the shoes, because another patient may choose to later. This would take a large amount of time to complete, because not only would all existing inventory need to be scanned, additional scans would need to be performed every time new inventory arrived.

By contrast, feature measurement and simulation according to the present disclosure involves foot measurements performed in one setting. That setting may be at home, at a doctor's office, or at a business such as a shoe store. Depending on the setting, the measurements include not only length and width but also account for angles between features of the foot and the way in which the person typically stands. Based on the collected measurements, the features of the foot are able to be mapped. The foot features may be mapped digitally, on paper, or both. Moreover, a shoe fit evaluator may be constructed. The shoe fit evaluator may then be used by the patient to accurately determine whether a particular pair of shoes will be a good fit for their foot or whether they should continue looking.

Figure 1A:
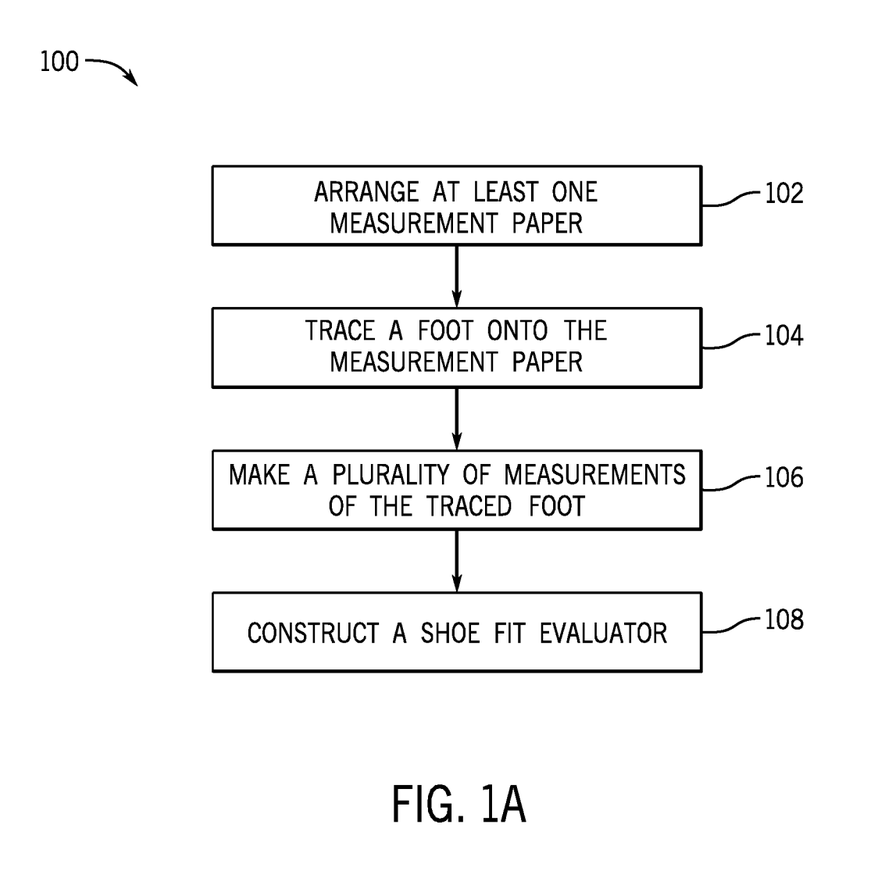
FIG. 1A is an example method for foot feature measurement and simulation consistent with the present disclosure.

FIG. 1A is an example method 100 for feature measurement and simulation consistent with the present disclosure. Method 100 may be performed entirely by a user in his or her own home and may be done using a kit purchased from a retail store, eliminating wait times between performing the measurements and receiving a shoe fit evaluator corresponding to the measured feature.

At 102, method 100 may include arranging at least one measurement paper. As used herein, a measurement paper refers to a specialized piece of paper with standardized measurements printed thereupon for use in feature measurement and simulation. The measurement paper is further discussed herein with respect to FIG. 1B. In some examples, arranging at least one measurement paper at 102 may include locating a level surface upon which to place the measurement paper. The measurement paper may then be removably fastened to the surface using, for example, tape, sticky tack, or any other removable fastener.

At 104, method 100 may include tracing a foot onto the measurement paper. As used herein, tracing refers to following and marking the outline of the foot, using a pen or pencil, onto a piece of paper such that, when the foot is removed, the outline remains. Tracing the foot at 104 may further include aligning the foot with lines on the measurement paper; these lines are further discussed herein with respect to FIG. 1B. The tracing may be performed by the user or by another person helping the user. Importantly, tracing the foot at 104 includes tracing around each individual toe and feature of the foot; this is imperative for the analysis of the tracing.

At 106, method 100 may include making a plurality of measurements on the traced foot, traced at 104. The measurements may include, for example, a variety of length measurements (e.g. length from heel to each toe) and width measurements at different points on the foot (e.g., at the heel, at the midpoint, at the portion of the foot just below the toes). In addition, measurements may further include measurements of different angles of the foot. For example, the angles of the toes may be measured, as may the angles of other points on the foot.

Based on, and using, the measurements taken at 106, a shoe fit evaluator may be constructed at 108. As used herein, a shoe fit evaluator refers to an implement made for the specific purpose of evaluating fit. In some cases, the shoe fit evaluator may be specifically made for the purpose of measuring the fit and suitability of a shoe, although examples are not so limited.

Figure 4A:
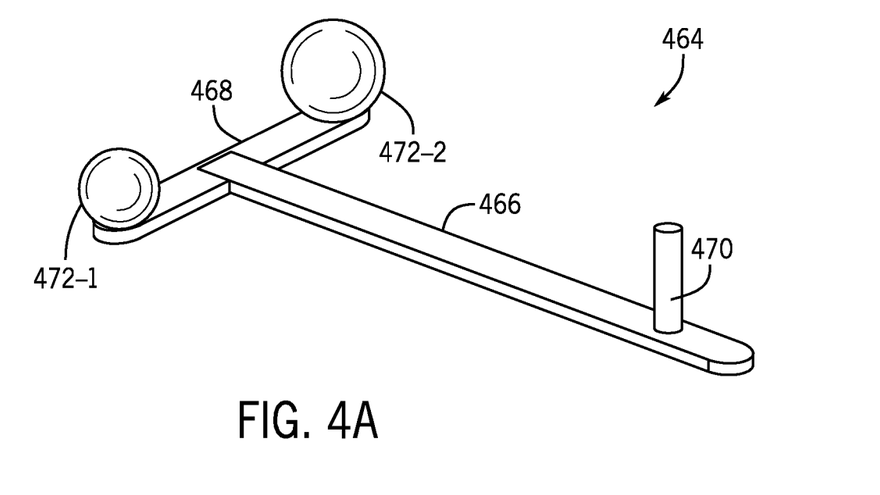
FIG. 4A is an example shoe fit evaluator constructed in accordance with the method of FIG. 1A.
Figure 4B:
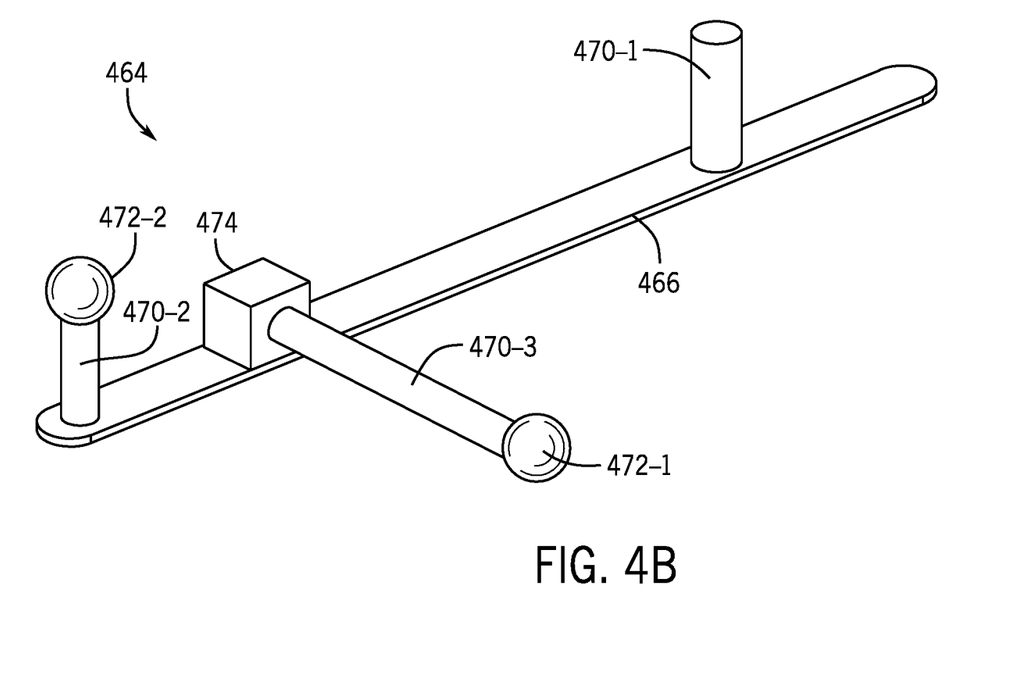
FIG. 4B is an example shoe fit evaluator constructed in accordance with the method of FIG. 1A.

In some examples, the shoe fit evaluator may be comprised of a series of rods and balls joined to one another. See, e.g. FIG. 4A and FIG. 4B. In FIGS. 4A and 4B, element 464 refers to the shoe fit evaluator, elements 466, 468, 470-N refer to the various rods, elements 472-N refer to the balls, and element 474 refers to another connection piece. In such examples, the diameter of the ball or balls may correspond to a shape or angle of a feature of the foot. That is, the particular diameter of a particular ball may be selected to correspond to a measurement of the foot, such that the shoe fit evaluator may represent the foot. In addition, the length of the rod or rods may correspond to a length or width of different portions of the foot. That is, the balls may be separated by rods corresponding to a taken length or width measurement of the foot, such that the location and separation of the balls corresponds to the actual location and separation of the corresponding features of the foot. In other examples, the shoe fit evaluator may include strips, which may be made of a flexible material, connection blocks, semi-spherical shapes (i.e., half circles), enclosures, or any other component or combination of components that may be used and able to simulate features of a foot. The balls and/or rods may be made of rigid plastic, metal, wood, or any other suitable material.

Figure 1B:
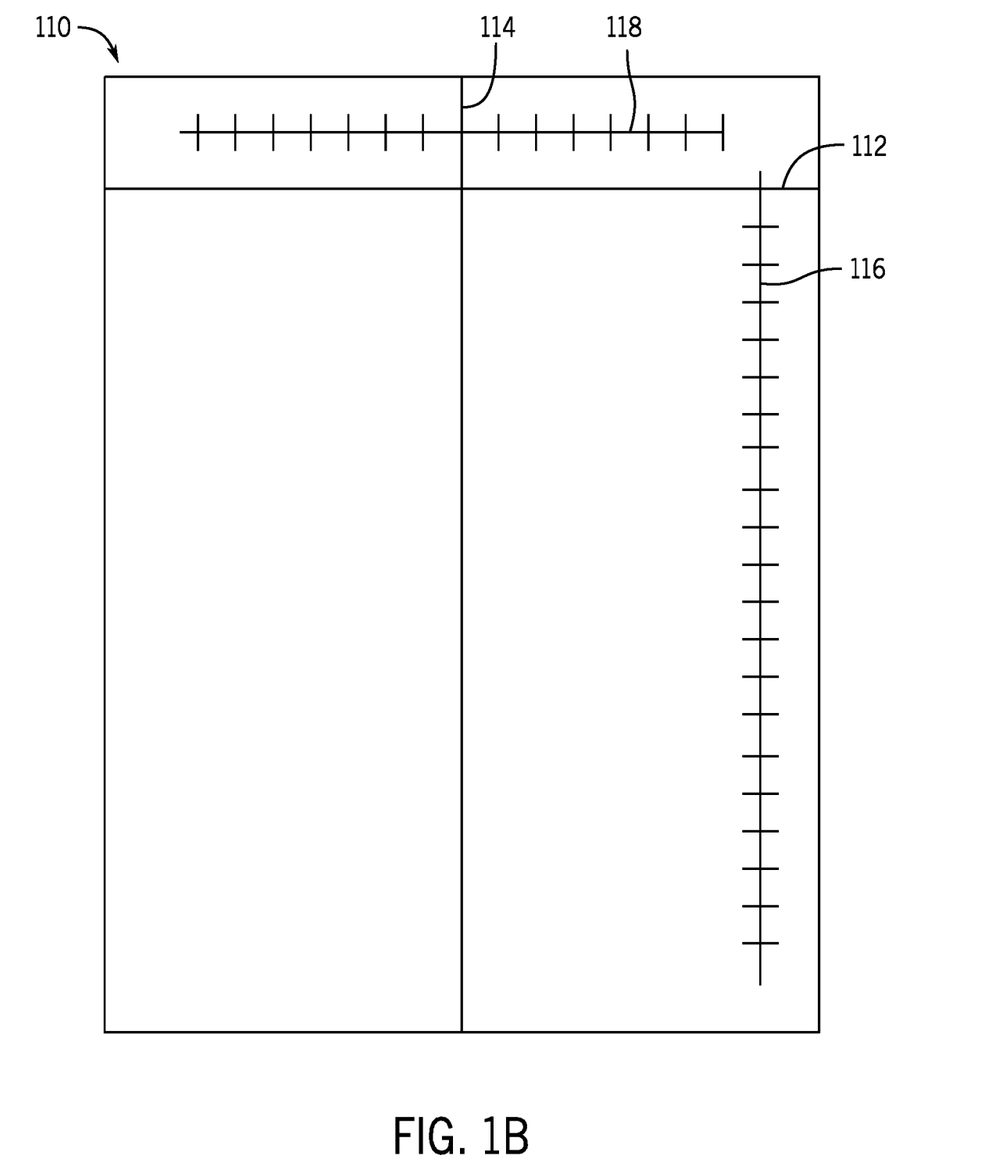
FIG. 1B is a measurement paper for use with the method of FIG. 1A.

FIG. 1B is a measurement paper 110 for use with the method of FIG. 1A. As shown in FIG. 1B, measurement paper 110 may be rectangular, although examples are not so limited and other shapes of paper may be used. Measurement paper 110 may include a plurality of placement lines 112 and 114. As used herein, a placement line refers to a line pre-printed onto measuring paper 110 to aid in proper placement of the foot before tracing. Placement line 112 may run horizontally and placement line 114 may run vertically such that placement line 112 intersects placement line 114. In such examples, the point of intersection may serve as a further indicator to aid in proper placement of the foot. Although only two placement lines are shown in FIG. 1B, examples are not so limited and more or fewer placement lines may be included.

Measuring paper 110 may further include a plurality of measurement rulers 116 and 118. Measurement rulers 116 and 118 may be located parallel to placement lines 112 and 114, respectively. As shown in FIG. 1B, measurement rulers 116 and 118 may be divided in regular increments, such as inches, centimeters, or a subdivision thereof (e.g., quarter inches or millimeters). Measurement rulers 116 and 118 may serve primarily as standardized points from which to make additional measurements of the traced foot. For example, measurement rulers 116 and 118 may provide a beginning or ending point for measurement of a length or width of the traced foot, or for measurement of an angle of a particular foot feature. Although only two measurement rulers 116 and 118 are shown in FIG. 1B, examples are not so limited and more or fewer measurement rulers may be included. In addition, although measurement rulers 116 and 118 are shown to be parallel to placement lines 112 and 114, examples are not so limited.

Figure 2A:
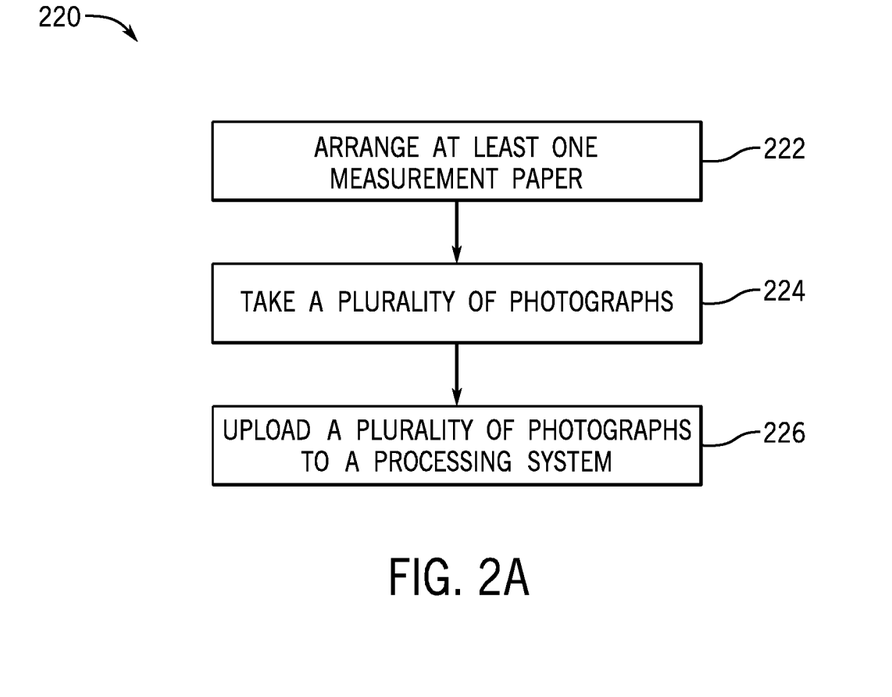
FIG. 2A is a method for foot feature measurement and simulation consistent with the present disclosure.

FIG. 2A is a method 220 for feature measurement and simulation consistent with the present disclosure. Method 220 may be performed entirely by a user in his or her own home. However, unlike method 100 (discussed with respect to FIG. 1A), the user may combine the at-home methodology with additional, off-site analysis. This may result in an improved and more customized shoe fit evaluator.

At 222, method 220 may include arranging at least one measuring paper. The measuring paper may be akin to measuring paper 110, discussed with respect to FIG. 1B. In some examples, arranging at least one measurement paper at 220 may include locating a level surface upon which to place the measurement paper. The measurement paper may then be removably fastened to the surface using, for example, tape, sticky tack, or any other removable fastener. In addition, arranging at least one measurement paper at 220 may include setting up appropriate lighting. This may include placing the measurement paper on a surface that is naturally well-lit by windows or by setting up lamps, overhead lights, or other artificial light sources.

At 224, method 220 may include taking a plurality of photographs. These photographs may be of the user's foot, as positioned on the measurement paper. The photographs may be taken using a mobile device, such as a cellular telephone or a tablet computer, or using a digital camera.

Taking a plurality of photographs at 224 may include taking a plurality of standardized photographs. Said differently, taking a plurality of photographs at 224 may include taking a series of photographs of the foot from different angles and from a set of known angles. In addition, the photographs may include an object of a known size, such as a coin, to aid in scaling of the photographs.

For example, one photograph of the plurality of photographs may be a top view photo of the foot on the measurement paper. Once the user has positioned his or her foot on the measurement paper, the user may then position a mobile phone on a tabletop or other surface having a known height above the floor, such that the camera of the mobile phone is pointing downwards towards the floor and thus, towards the foot and camera. Then, the user may take a photo of his or her foot, with the measuring paper as the background. This process may be repeated for each foot, and may be done multiple times for each foot, using different angles (e.g., from the side). However, examples are not so limited, and other methods of taking photographs may be used.

In addition, taking photographs at 224 may include receiving guidance for how to properly take the photographs. This may include watching a video associated with an off-site analysis website, reviewing an instruction booklet included with the measurement paper and accompanying kit, or receiving step-by-step instructions through, for example, a mobile phone application that is downloaded by the user.

At 226, method 220 may include uploading the plurality of photographs to a website. The website may be an off-site analysis website, such that uploading the photographs taken at 224 will allow for further analysis and simulation of the features of the foot. In some examples, the photographs may be uploaded directly to the website from the mobile device or camera used to take the photographs. In other examples, the photographs may be uploaded using a mobile application. This may particularly be used if a mobile application is used to guide the taking of the photographs at 224. Once the photographs are uploaded at 226, the user-end portion of the feature measurement and simulation is concluded.

Figure 2B:
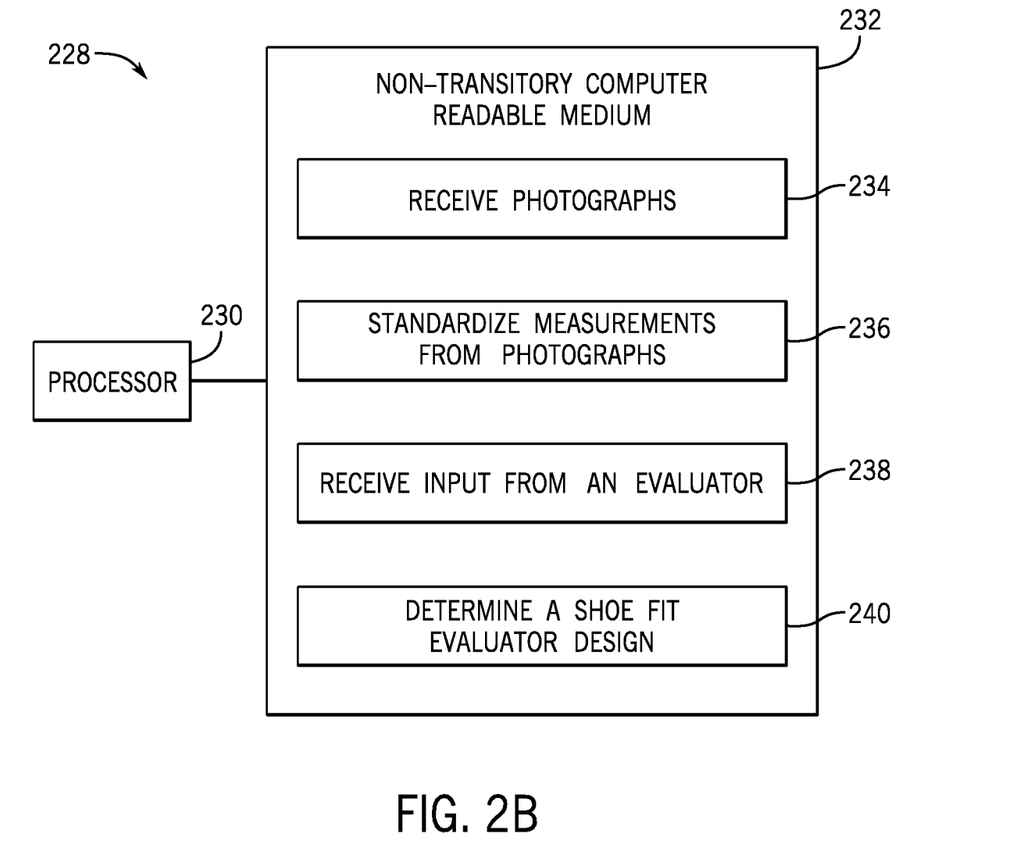
FIG. 2B is a system for foot feature measurement and simulation consistent with the present disclosure

FIG. 2B is a system 228 for feature measurement and simulation consistent with the present disclosure. System 228 may be used in conjunction with method 220, discussed with respect to FIG. 2A. More particularly, system 228 may correspond to additional, off-site analysis of the at-home methodology of method 220.

System 228 may include a processor 230. Processor 230 may be one or more central processing units (CPUs), microprocessors, and/or other hardware devices suitable for retrieving and executing instructions stored on a storage medium. As an alternative, processor 230 may include one or more electronic circuits containing a number of electronic components for performing functionality of the stored instructions.

System 228 may further include a non-transitory computer readable medium 232. Processor 230 may be coupled to a non-transitory computer readable medium 232. As used herein a non-transitory computer readable medium may be any electronic, magnetic, optical, or other physic storage device that stores executable instructions. Thus, non-transitory computer readable medium 232 may be, for example, RAM, an Electronically-Erasable Programmable Read-Only Memory (EEPROM), a storage drive, an optical disc, and the like. Non-transitory computer readable storage medium 232 may be disposed within a system, such as is shown in FIG. 2B. Non-transitory computer readable medium 232 may further be a portable, external, or remote storage medium that allows processor 230 to download instructions from said storage medium. Non-transitory computer readable medium 232 may contain instructions, such as instructions 234, 236, 238 and/or 240, that may be executable by a processor such as processor 230, for feature measurement and simulation.

Instructions 234, when executed by a processor such as processor 230, may include instructions to receive a plurality of photographs. The received plurality of photographs may correspond to the photographs taken at step 224 of method 220, discussed with respect to FIG. 2A, and may be the photographs uploaded for processing at step 226. As discussed with respect to FIG. 2A, the photographs taken may be uploaded directly to a website or be uploaded by a mobile application. However, instructions 234 may receive the plurality of photographs regardless of the method used to upload the photographs.

Instructions 236, when executed by a processor such as processor 230, may include instructions to standardize a plurality of measurements from the received plurality of photos. As used herein, to standardize a plurality of measurements refers to a process of performing a particular set of measurements of the foot in the photograph, using a known and standard set of measurement units. Instructions 236 may include instructions to measure a plurality of features on the foot; these features may include, but are not limited to, length of the foot, width of the foot at different locations, and various angles of the foot. In some examples, the standardized set of measurements may use the object of known size in the picture (discussed with respect to FIG. 2A), and/or the measurement lines on the measurement paper, to provide a reference set of measurements.

Instructions 236 may further include instructions to standardize additional measurements provided by the user. In some examples, the user may make some measurements that are then uploaded along with the photographs. These user-made measurements may be less precise than digitally-made measurements; however, they may be used to provide a baseline set of measurements. The standardization of the measurements at 236 may then be done by refining the user-provided measurements.

Instructions 238, when executed by a processor such as processor 230, may include instructions to receive input from an evaluator. As used herein, an evaluator refers to an entity who reviews the measurements and photographs, as well as any additional information provided by the user, to further refine the analysis of the photographs and thus of the user's foot and associated problems. The evaluator may be a medical doctor, a nurse, or anyone else who has received training to review and provide additional input and analysis of the photographs and measurements. In some examples, the evaluator may be a virtual evaluator. Said differently, the evaluator may be a software program designed to evaluate photographs and measurements using flowchart and decision tree analysis, Artificial Intelligence (AI), or any other type of digital or virtual evaluator.

In some examples, the evaluator may input additional features or variables that may affect the analysis of the foot and thus, may affect the design of a shoe fit evaluator. For example, a user may have a feature, such as a corn or bunion, on one or more toes. This feature may be visible on the photographs but may not be in a position to affect the standardization of measurement at instructions 236. However, the existence of such a feature may affect the fit and/or comfort of shoes, and thus should be accounted for when designing a shoe fit evaluator for the user. The evaluator, therefore, may input the existence of the feature, as well as any measurements they can make, such that the input is received at instructions 238. As a result, the measuring device will be designed to include this feature, thus resulting in having a more robust and accurate measuring device. Examples are not so limited, however, and other inputs may be made by an evaluator.

Instructions 240, when executed by a processor such as processor 240, may include instructions to determine a shoe fit evaluator design. As discussed with respect to FIG. 1A, a shoe fit evaluator refers an implement made for the specific purpose of evaluating fit, particularly of a shoe. Instructions 240 may include instructions to compile the received photographs, standardized measurements, and received input from the evaluator to determine the features that should be included in a shoe fit evaluator. This may further include determining the length of rods to be used, the diameter of balls to be used for simulation of various features, and the angles at which the rods and balls should be disposed with respect to each other.

In some examples, the designed shoe fit evaluator may then be manufactured. The shoe fit evaluator may be manufactured using off-the-shelf parts; however, examples are not so limited, and the shoe fit evaluator may be manufactured through computer numerical control (CNC) machining, three dimensional (3D) printing, or any combination thereof. The manufacture of the shoe fit evaluator may occur on-site, i.e., at the same location where the analysis occurs, and may then be sent to the user. In other examples, the design of the shoe fit evaluator, perhaps together with the parts, may be sent to a store location (such as the location where the user purchased a kit to perform the method); the shoe fit evaluator may then be constructed at the store for pick-up by the user. In still other examples, the shoe fit evaluator design, including dimension details, may be transmitted to a store, such as a shoe store, that has an evaluator-making kit. The evaluator-making kit may consist of a set of interconnecting parts for use in constructing a shoe fit evaluator, such a rods, balls, and the like. When the shoe fit evaluator design is received by the store, the store may construct a temporary shoe fit evaluator for use by the user. The user may then utilize the shoe fit evaluator to test the fit and suitability of shoes being considered for purchase. Then, once the user has selected a pair of shoes, the temporary shoe fit evaluator may be disassembled into its component parts, such that the parts are ready and able to be used to construct similar temporary shoe fit evaluators for other users. In some examples, the store may be an online shoe retailer; the retailer may construct the temporary shoe fit evaluator and use it to test a pair of shoes specified by the user. Based on whether the shoe fit evaluator indicates that the pair of shoes is a good fit, the online retailer may let the customer know that their desired shoe selection may cause foot problems and recommend an alternate pair of shoes. In this way, the online retailer is able to reduce the number of shoes returned for being ill-fitting.

Figure 3A:
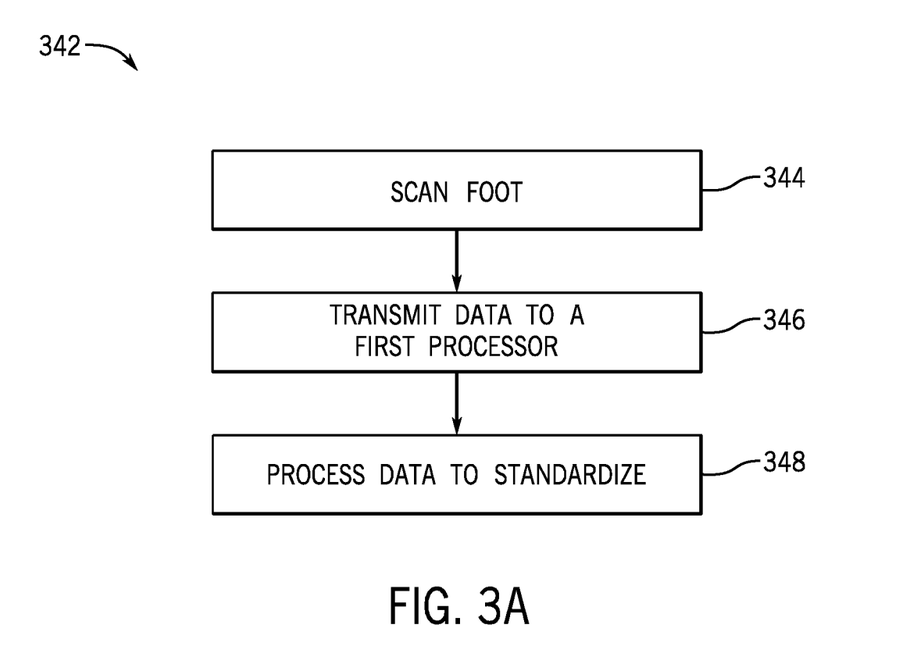
FIG. 3A is a method for foot feature measurement and simulation consistent with the present disclosure.

FIG. 3A is a method 342 for feature measurement and simulation consistent with the present disclosure. Unlike methods 100 and 220, discussed with respect to FIGS. 1A and 2A, respectively, method 342 may be performed entirely outside of the user's home. Instead, method 342 may be performed in a doctor's office or at a store, such a shoe store.

At 344, method 342 may include scanning a foot. The foot may be scanned electronically using, for example, a Coordinate Measuring Machine ("CMM"), a laser-based scanner, or any other digital or electronic scanner. The foot may further be scanned from multiple angles or in multiple positions. For example, the foot may be scanned from the top, bottom, and side, and may be scanned with the user both standing normally and while balancing on the foot being scanned. In addition, the user may be instructed to move or place pressure on different parts of their foot (e.g., put their weight in their heels, shift towards the ball of their foot).

At 346, method 342 may include transmitting the data associated with the scan performed at 344 to a first processor. The first processor may be located in the same location as the location of the scan (i.e., within the doctor's office or store) or may be off-premises. In some examples, the data may be transmitted to a first processor at the same location as the scan for initial processing and analysis, and then may be transmitted to a second processor for further processing (discussed herein with respect to FIG. 3B).

At 348, method 342 may include processing the data associated with the scan. This may be performed at the processor to which the data was transmitted at 346. In some examples, processing the data associated with the scan may include standardizing the data. For example, the data may be processed into a different coordinate system (e.g., converted from Cartesian coordinates to polar coordinates), or if multiple scans were performed, the individual scans, and the associated data, may be integrated into a single set of data.

Figure 3B:
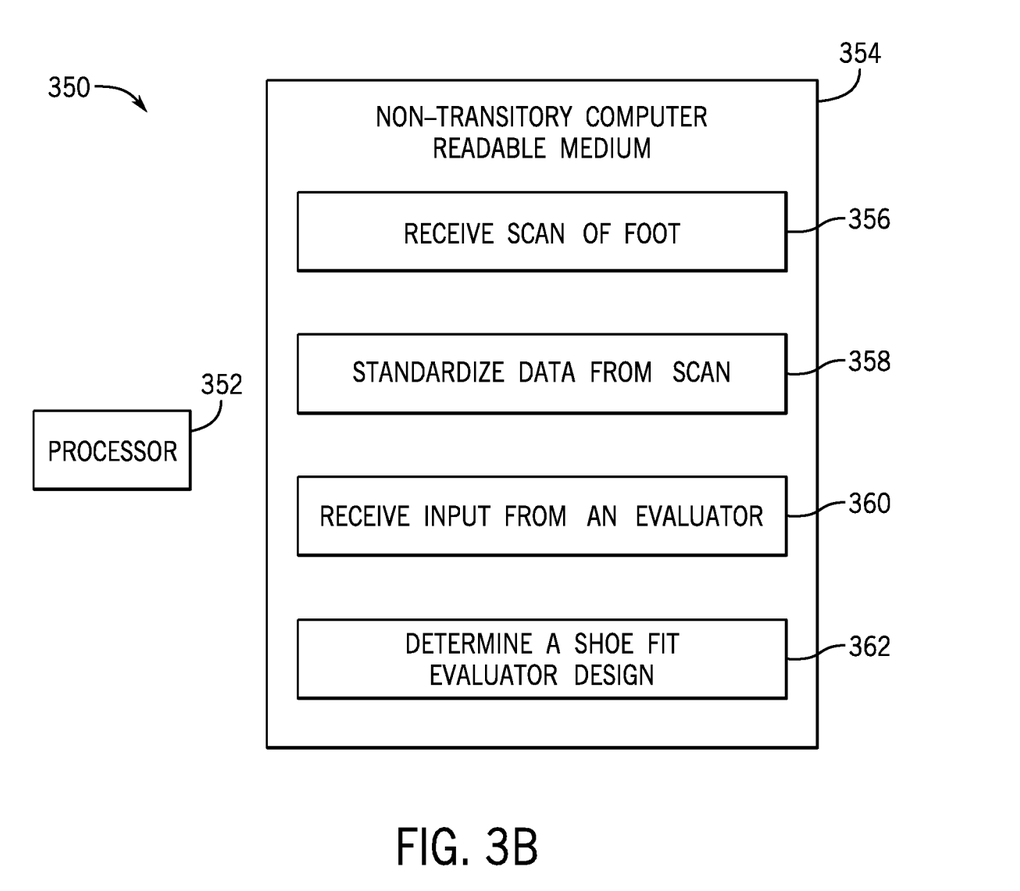
FIG. 3B is a system for foot feature measurement and simulation consistent with the present disclosure.

FIG. 3B is a system 350 for feature measurement and simulation consistent with the present disclosure. System 350 may be used in conjunction with method 342, discussed with respect to FIG. 3A. More particularly, system 350 may correspond to additional, off-site analysis of the methodology of method 342.

System 350 may include a processor 352. Processor 352 may be one or more central processing units (CPUs), microprocessors, and/or other hardware devices suitable for retrieving and executing instructions stored on a storage medium. As an alternative, processor 352 may include one or more electronic circuits containing a number of electronic components for performing functionality of the stored instructions.

System 350 may further include a non-transitory computer readable medium 354. Processor 352 may be coupled to a non-transitory computer readable medium 354. As used herein a non-transitory computer readable medium may be any electronic, magnetic, optical, or other physic storage device that stores executable instructions. Thus, non-transitory computer readable medium 354 may be, for example, RAM, an Electronically-Erasable Programmable Read-Only Memory (EEPROM), a storage drive, an optical disc, and the like. Non-transitory computer readable storage medium 354 may be disposed within a system, such as is shown in FIG. 3B. Non-transitory computer readable medium 354 may further be a portable, external, or remote storage medium that allows processor 352 to download instructions from said storage medium. Non-transitory computer readable medium 354 may contain instructions, such as instructions 356, 358, 360, and/or 362, that may be executable by a processor such as processor 352, for feature measurement and simulation.

Instructions 356, when executed by a processor such as processor 352, may include instructions executable to receive a scan of a foot. In some examples, the received scan may be the scan taken at 344 of method 342, discussed with respect to FIG. 3A. The received scan may be pre-processed (e.g., may be the standardized data from FIG. 3A) or may be the raw data from the scan performed at 344.

Instructions 358, when executed by a processor such as processor such as processor 352, may include instructions executable to standardize the data associated with the scan, as received at 356. Instructions 358 may include instructions to measure a plurality of features on the foot; these features may include, but are not limited to, length of the foot, width of the foot at different locations, and various angles of the foot. In some examples, the standardized set of measurements may be directly taken from the scan. In other words, the scan may be analyzed and measurements may be taken based on the analysis.

Instructions 360, when executed by a processor such as processor such as processor 352, may include instructions executable to receive input from an evaluator. As discussed with respect to FIG. 2B, the evaluator may review the scans and measurements and photographs, as well as any additional information provided by the user, to further refine the analysis of the scans and thus of the user's foot and associated problems.

In some examples, the evaluator may analyze the scan to, for example, determine a diagnosis or design recommendation for the user. For instance, by looking at the scans in conjunction with the standardized data and any measurements made, an evaluator may be able to determine that a user's foot (or a specific portion thereof) has depths in some locations that are higher than average, lower than average, or at a slightly different location than would be considered a "normal" location. Based on the analysis of the scan, the user may be noted to have any number of conditions. For example, analysis of the scan may reveal that a user has a higher than average or lower than average arch depth, a tendency to supinate or pronate the foot, and/or any number of maladies related to the metatarsals, including, but not limited to, rotated toes (e.g., hammer toe), metatarsalgia, hallux valgus (i.e. bunions), and claw toe. Based on these conditions, the evaluator may make specific design recommendations to properly account for these conditions.

Instructions 362, when executed by a processor such as processor 352, may include instructions executable to design a shoe fit evaluator. As discussed with respect to FIGS. 1B and 2B, the shoe fit evaluator may be an implement to measure the fit of a shoe. Instructions 362 may include instructions to compile the received scans, standardized measurements, and received input from the evaluator to determine the features that should be included in a shoe fit evaluator. This may further include determining the length of rods to be used, the diameter of balls to be used for simulation of various features, and the angles at which the rods and balls should be disposed with respect to each other. In some examples, the shoe fit evaluator may be comprised of a series of rods and balls joined to one another. In other examples, the shoe fit evaluator may include strips, which may be made of a flexible material, connection blocks, semi-spherical shapes (i.e., half circles), enclosures, or any other component or combination of components that may be used and able to simulate features of a foot. In some examples, the shoe fit evaluator may be manufactured using off-the-shelf parts; however, examples are not so limited, and the shoe fit evaluator may be manufactured through computer numerical control (CNC) machining, three dimensional (3D) printing, or any combination thereof.

When in use, the shoe fit evaluator may be inserted into a shoe to check the fit of the shoe relative to the particular feature, or features, represented by the measurement device. This may aid in selection of properly fitting shoes without the need to scan the interiors of every shoe being considered. For example, FIG. 4A is an example shoe foot evaluator 464 designed to measure a particular foot feature, and FIG. 4B is an example of a second shoe fit evaluator 464 designed to measure a different particular foot feature. In both examples, however, as well as with any other shoe foot evaluator constructed, the shoe fit evaluator is inserted into the shoe that is being tested for fit with the particular foot feature. Once the shoe fit is judged, the shoe fit evaluator is removed.

In some examples, the shoe fit evaluator may further include an indicator. The indicator may be integrated with the shoe fit evaluator or may be removably coupled thereto. One indicator may be a pressure indicator. The pressure indicator may be located on the measuring device at a location where a shoe is most likely to exert pressure on the foot; this location may be determined through analysis of the mapped features. When the shoe fit evaluator is inserted into a shoe, the pressure indicator may detect an amount of pressure being exerted by the shoe and, based on the amount of pressure, provide an indication. If the amount of pressure is greater than an accepted amount of pressure (as determined by the feature simulator), the indicator may give an indication; if the amount of pressure is less than the accepted amount of pressure, no indication may occur. The indication may be audible, such as a buzz, beep, or other noise, visible, such as a Light-Emitting Diode (LED) flashing, or any other type of suitable indication that would alert a patient that the shoe being considered is not a good option.

In some examples, the indicator may be an electronic switch system. In such examples, a switch body may be electrically coupled to a circuit board. A switch button may cover the switch body, and may be selectively depressed. The circuit board may have a plurality of electrical components, including, but not limited to, a battery, a plurality of resistors, a plurality of capacitors, and/or a piezoelectric indicator. The circuit board may also include a speaker to sound an audible tone when the switch button is depressed. That is, depressing the switch button may complete a circuit that includes an indicator coupled to the speaker, such that the audible tone sounds when the switch button is depressed. This may serve to indicate to a user that the shoe the measuring device is being used to measure exerts too much pressure and thus will not be a good option for the patient.

The switch body and switch housing (collectively, the "switch") may be coupled to the measuring device. In some examples, the switch may be at a location that corresponds to a particular feature; in other examples, the switch may be at a location that does not correspond to a particular feature. The switch may be located at a first end of the shoe fit evaluator, and may be coupled to a circuit board located at a second end of the shoe fit evaluator. In such examples, the circuit board may be located at or within a handle of the shoe fit evaluator. This may aid in utilization of the shoe fit evaluator and remove bulk from the actual measuring portion, allowing the shoe fit evaluator to retain its accuracy while still providing additional indications via the switch to a user.

In the foregoing detailed description of the present disclosure, reference is made to the accompanying drawings that form a part hereof, and in which is shown by way of illustration how examples of the disclosure may be practiced. These examples are described in sufficient detail to enable those of ordinary skill in the art to practice the examples of this disclosure, and it is to be understood that other examples may be utilized and that process, electrical, and/or structural changes may be made without departing from the scope of the present disclosure.

The figures herein follow a numbering convention in which the first digit corresponds to the drawing figure number and the remaining digits identify an element or component in the drawing. Elements shown in the various figures herein can be added, exchanged, and/or eliminated so as to provide a number of additional examples of the present disclosure. In addition, the proportion and the relative scale of the elements provided in the figures are intended to illustrate the examples of the present disclosure, and should not be taken in a limiting sense. Further, as used herein, "a number of an element and/or feature can refer to one or more of such elements and/or features.

What is claimed is:

1. A method, comprising:
arranging a measurement paper;
tracing a foot onto the measurement paper;
making a plurality of measurements on the traced foot; and
constructing, based on the plurality of measurements on the traced foot, a shoe fit evaluator comprising a plurality of shoe fit evaluator pieces including a plurality of balls and rods, by:
determining the length of the rods to be used, the diameter of the balls to be used for simulation of various features, and the angles at which the rods and the balls should be disposed with respect to each other;
selecting the plurality of shoe fit evaluator pieces; and
joining the selected shoe fit evaluator pieces to simulate the at least one feature of the foot.

2. The method of claim 1, wherein tracing a foot onto the measurement paper further comprises:
positioning the foot on the measurement paper such that the foot is aligned with a plurality of lines on the measurement paper; and
tracing each feature of the foot.

3. The method of claim 1, wherein making a plurality of measurements on the traced foot further comprises:
measuring a length of the traced foot;
measuring a width of the traced foot; and
measuring a plurality of angles of features of the traced foot.

4. The method of claim 1, further comprising:
inserting the shoe fit evaluator into a shoe to check the fit of the shoe relative to the at least one feature of the foot.

5. A method, comprising:
arranging a measurement paper;
taking a plurality of photographs of a foot, wherein the foot is placed on the measurement paper; and
uploading the plurality of photographs to a processing system, wherein the system further comprises:
a processor; and
a non-transitory computer readable medium including instructions executable by the processor to:
receive the plurality of photographs of the foot;
standardize a plurality of measurements from the plurality of photographs to determine a standardized set of measurements;
receive input from an evaluator; and
compiling the received photographs, the standardized set of measurements, and the input received from the evaluator; and
determine a design for a shoe fit evaluator wherein the shoe fit evaluator consists of a plurality of interconnecting structural components comprising a plurality of shoe fit evaluator pieces including a plurality of balls and rods, and the shoe fit evaluator simulates at least one feature of the foot, by:
determining the length of the rods to be used, the diameter of the balls to be used for simulation of various features, and the angles at which the rods and the balls should be disposed with respect to each other;
executing the instructions by the processing system and determining the design for the shoe fit evaluator; and
manufacturing the shoe fit evaluator by:
selecting the plurality of shoe fit evaluator pieces; and
joining the selected shoe fit evaluator pieces to simulate the at least one feature of the foot.

6. The method of claim 5, wherein taking a plurality of photographs of a foot further comprises:
arranging the foot on the measurement paper;
arranging a reference object of known dimension; and
taking a plurality of photographs of the foot from a known angle.

7. The method of claim 5, wherein the instructions to standardize a plurality of measurements from the plurality of photographs further comprises measuring a plurality of features on the foot, wherein the plurality of features include:
a length of the foot;
a width of the foot; and
an angle of the foot.

8. The method of claim 5, wherein the instructions to receive input from an evaluator further comprises:
analyzing the plurality of photographs in view of additional information provided by a user; and
inputting additional information for processing and use in design of a shoe fit evaluator.

9. The method of claim 5, wherein executing the instructions by the processing system and determining the design for the shoe fit evaluator comprises:
determining a plurality of features of the foot, wherein determining a plurality of features of the foot further comprises:
determining a relationship between at least two features of the foot; and
designing the shoe fit evaluator to represent the relationship.

10. The method of claim 5, further comprising:
inserting the shoe fit evaluator into a shoe to check the fit of the shoe relative to the at least one feature of the foot.

11. A method, comprising:
scanning a foot;
transmitting data of the scan to a first processor;
processing the data at the first processor to standardize the data; and
uploading the scan to a processing system, wherein the system further comprises:
a second processor; and
a non-transitory computer readable medium including instructions executable by the second processor to:
receive the scan of the foot;
standardize data from the scan;
receive input from an evaluator; and
determine a design for a shoe fit evaluator, wherein the shoe fit evaluator consists of a plurality of interconnecting structural components comprising a plurality of shoe fit evaluator pieces including a plurality of balls and rods, and the shoe fit evaluator simulates at least one feature of the foot, by:
determining the length of the rods to be used, the diameter of the balls to be used for simulation of various features, and the angles at which the rods and the balls should be disposed with respect to each other;

executing the instructions by the processing system and determining the design for the shoe fit evaluator; and manufacturing the shoe fit evaluator by:
  selecting the plurality of shoe fit evaluator pieces; and
  joining the selected shoe fit evaluator pieces to simulate the at least one feature of the foot.

12. The method of claim 11, wherein scanning the foot comprises scanning the foot using a Coordinate Measurement Machine (CMM).

13. The method of claim 11, wherein processing the data at the first processor further comprises:
  translating the data into a particular coordinate system; and
  integrating data from multiple scans into a single set of data.

14. The method of claim 11, wherein the instructions to standardize data from the scan further comprises measuring a plurality of features of the foot from the scan, wherein the features comprise:
  a length of the foot;
  a width of the foot; and
  a plurality of angles of the foot.

15. The method of claim 11, wherein the instructions to receive input from the evaluator further comprises receiving a diagnosis associated with at least one feature of the foot.

16. The method of claim 11, wherein the instructions to determine a design for a shoe fit evaluator further comprise:
  receiving standardized plurality of measurements, wherein the standardized plurality of measurements correspond to the standardized data;
  receiving the input from the evaluator; and
  determining a plurality of features of the foot, wherein determining a plurality of features of the foot further comprises:
    determining a relationship between at least two features of the foot; and
    designing the shoe fit evaluator to represent the relationship between the features.

17. The method of claim 16, wherein designing a shoe fit evaluator further comprises determining a location for an indicator to be included in the shoe fit evaluator.

18. The method of claim 11, further comprising:
  inserting the shoe fit evaluator into a shoe to check the fit of the shoe relative to the at least one feature of the foot.

* * * * *